(12) United States Patent
Lindemann et al.

(10) Patent No.: US 6,325,795 B1
(45) Date of Patent: Dec. 4, 2001

(54) REPLACEABLE ACCESSORY CORD AND HANDSWITCH

(75) Inventors: Russell Wayne Lindemann, Longmont; David Nichols Heard, Boulder, both of CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/378,931

(22) Filed: Aug. 23, 1999

Related U.S. Application Data

(63) Continuation-in-part of application No. 08/897,404, filed on Jul. 21, 1997, which is a continuation of application No. 08/614,122, filed on Mar. 12, 1996, now abandoned.

(51) Int. Cl.$^7$ .................................................. A61B 18/18
(52) U.S. Cl. ............................ 606/32; 606/41; 200/293.1
(58) Field of Search ........................... 606/32–35, 37–42, 606/45–50; 200/293.1, 295, 329, 332.2

(56) References Cited

U.S. PATENT DOCUMENTS

| | | |
|---|---|---|
| 3,494,363 | 2/1970 | Jackson . |
| 3,752,160 | 8/1973 | Billin . |
| 4,370,980 | 2/1983 | Lottick . |
| 4,552,143 * | 11/1985 | Lottick .................................. 606/49 |
| 5,196,007 * | 3/1993 | Ellman et al. ......................... 606/32 |
| 5,304,763 * | 4/1994 | Ellman et al. ....................... 200/295 |

\* cited by examiner

*Primary Examiner*—Michael Peffley

(57) ABSTRACT

A replaceable accessory cord and hand switch set for an electrosurgical instrument wherein the accessory cord electrically couples an electrosurgical generator to the electrosurgical instrument. The hand switch is electrically coupled with the accessory cord. A button on the hand switch activates the flow of electrosurgical current in the instrument. An insulated mechanical connector on the hand switch conforms and adheres to the electrosurgical instrument, mounting the hand switch thereon, and preventing longitudinal, lateral, and circumferential movement therebetween. The hand switch is positioned on the electrosurgical instrument for easy access and control by the surgeon's finger.

14 Claims, 11 Drawing Sheets

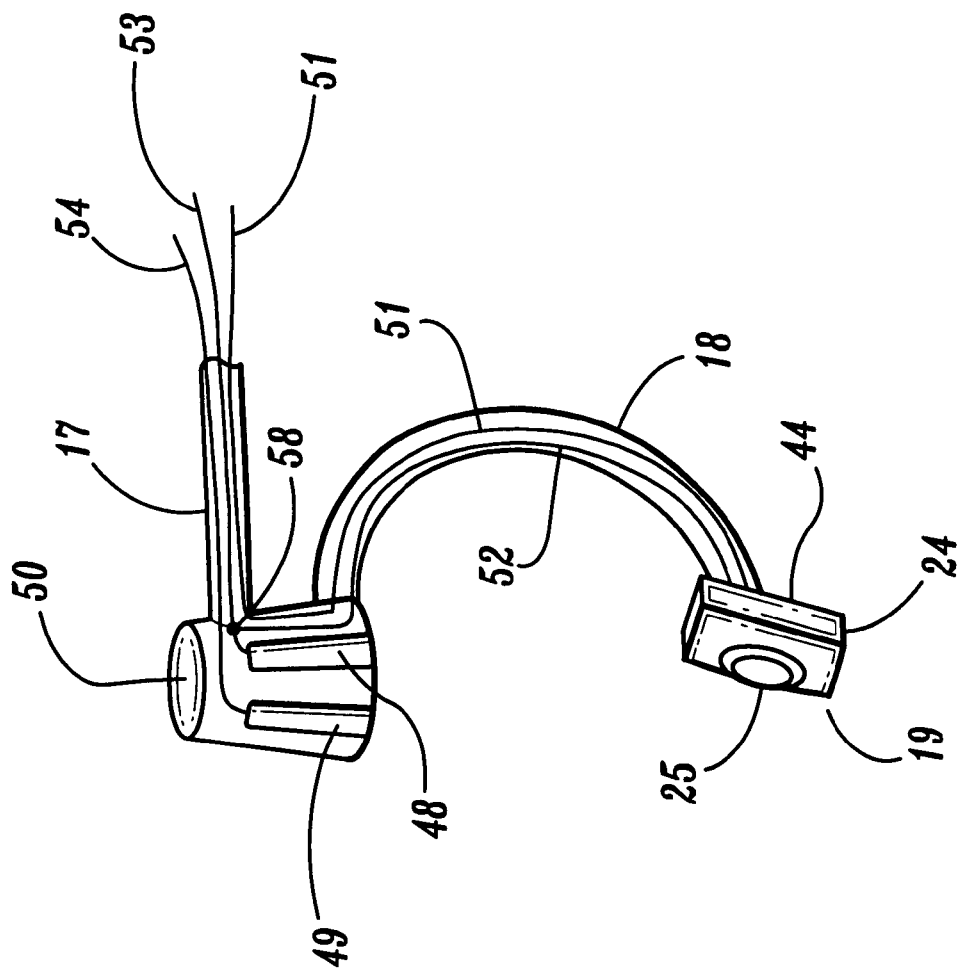

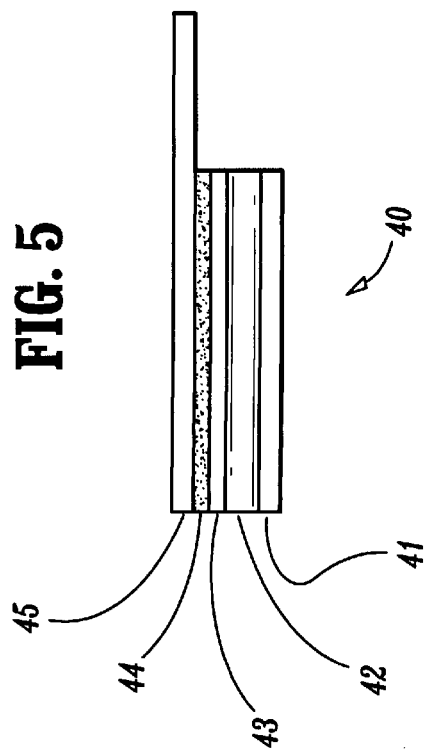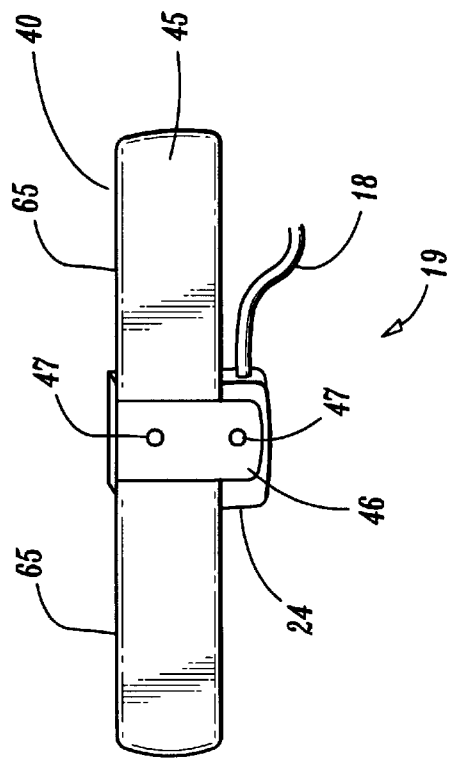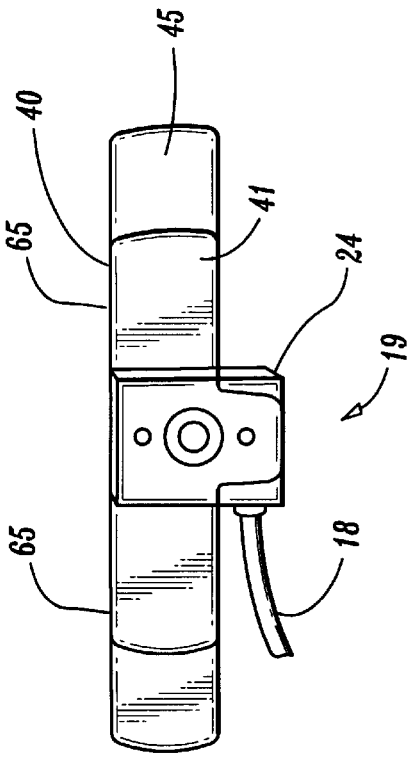

REPLACEABLE ACCESSORY CORD AND HANDSWITCH

RELATED APPLICATION

This application is a continuation-in-part of application Ser. No. 08/897,404 filed Jul. 21, 1997 which is a continuation of application Ser. No. 08/614,122 filed on Mar. 12, 1996.

BACKGROUND

1. Technical Field

This disclosure relates to a replaceable accessory cord and hands witch set for use with an electrosurgical instrument having no hands witch. More particularly, the replaceable accessory cord connects with the terminal of the electrosurgical instrument and the hands witch attached to the replaceable accessory cord mounts conveniently on the electrosurgical instrument, so the hands witch is accessible to the surgeon controlling the electrosurgical current delivery to a patient.

2. Description of the Related Art

Any electrosurgical instrument, such as scissors, graspers, a forceps, and the like, receives elecrosurgical current from an electrosurgical generator. A remote foot switch or hand switch connected to the electrosurgical generator normally controls the application of electrosurgical current to the electrosurgical instrument. Surgeons frequently prefer the convenience of using a hand switch. Since one hand of the surgeon holds the electrosurgical instrument, the finer actuation of a switch mounted on the electrosurgical instrument is convenient.

To minimize the cost of such electrosurgical instruments, suppliers frequently provide them without an integral hands witch for use by the surgeon. That omission benefits cleanability and sterilization after use if the electrosurgical instrument is reusable (as sterilization would ruin the hands witch circuitry), and minimizes replacement cost if the electrosurgical instrument is disposable. Consideration of the addition of a convenient finger switch may not be worth added expense.

Control of high frequency electrosurgical current at the electrosurgical instrument has long been a problem addressed in many ways. The use of fluidic control disclosed in U.S. Pat. No. 3,494,363 teaches squeezing a bulb or closing a vacuum port by the surgeon to control electrosurgical current delivery to a forceps. U.S. Pat. No. 3,752,160 is a disposable electrode switch attached to a forceps and functional when the tines are squeezed together. In particular, the electrosurgical current is transmitted in a monopolar application when a terminal on the cord contracts bare metal on the forceps.

Removable hands witches for electrocautery instruments have been described in U.S. Pat. No. 4,370,980 and 4,552,143. Conductive spring clips attach the hands witches to an electrosurgical instrument such as scissors, graspers, or a forceps. The electrically wired hands witch allows current passage through electrically conductive clips for attachment to the electrosurgical instrument. Cutting or cauterizing electrosurgical current passing through the hands witch depends on the operation of the button by the surgeon. Insulated handles of the electrosurgical instrument protect the surgeon from the electrosurgical current, but nothing protects the surgeon from the exposed conductive spring clips. U.S. Pat. No. 5,196,007 discloses a hands witch for use in conjunction with electrosurgical instruments with several types of mounts for attachment. These mounting methods include a tubular clip, Velcro®, tie straps, and dual clips for conjunction with slotted receptacles.

There has been a need to convert existing standard electrosurgical instruments such as "Endopath" instruments by Johnson & Johnson or the "Endo" products of United States Surgical Corporation to hand switching with a simple and low cost replaceable accessory cord and hands witch set. No combination of a replaceable accessory cord and hands witch set substitutes for the regular cord set by electrically coupling the electrosurgical generator and the electrosurgical instrument connects to and additionally affording finger switching on the electrosurgical instrument. No replaceable cord and hands witch set provides universal mounting capability to support a nonintegral hands witch button. No replaceable cord and hands witch set provides an attached hands witch for finger actuation of the switch button adhesively mountable on any reusable or disposable electrosurgical instrument. No replaceable cord and hands witch set provides secure attachment of the hands witch to the electrosurgical instrument by means of a mount or support resistant to longitudinal, lateral, or circumferential movement relative to the electrosurgical instrument.

SUMMARY

A replaceable accessory cord and hands witch set is provided for use with conventional electrosurgical instruments which are not manufactured with resident switches for activation or electrosurgical current. The accessory cord may carry electrosurgical current to the electrosurgical instrument from an electrosurgical generator. The accessory cord may connect with a hands witch, which can include a small button, for activation of the electrosurgical current.

Attached to the switch is a mechanical connector for universal mounting on and attachment to electrosurgical instruments. The mechanical connector may have two adjustable wing-like extensions which wrap around and conform to various parts and surfaces of any electrosurgical instrument. The mechanical connector may be composed of a laminate of a malleable metal and an adhesive, the metal providing tear resistance and stiffness as well as bendability and conformability, and in conjunction with the adhesive, preventing longitudinal, lateral, or circumferential movement of the hands witch relative to the instrument. The mechanical connector can allow for convenient activation of electrosurgical current by the surgeon pressing the button with a finger. The mechanical connector may electrically insulate the hands witch from the instrument preventing leakage, stray current, or grounding by the surgeon.

Alternate embodiments of the replaceable accessory cord provide connections for monopolar and bipolar instruments, as well as varied male or female plug connectors for use with differing models and brands of electrosurgical generators and electrosurgical instruments. The accessory cord may be configured to plug into a footswitch outlet on electrosurgical generator models not equipped with hands witch connections. Additionally, the hands witch may have additional switches for selective activation of different types of electrosurgical waveforms (e.g. cut or coagulation).

Another embodiment comprises the hands witch and mechanical connector described wherein the hands witch connects with a jumper connector for use with a reusable accessory cord. The jumper connector would connect between the reusable accessory cord and the electrosurgical instrument.

BRIEF DESCRIPTION OF THE DRAWINGS

Various embodiments of the present disclosure are described with reference to the drawings herein:

FIG. 2 is a perspective view with partial cutaway showing a replaceable accessory cord and hands witch set of an alternate embodiment wherein the switch is separate from the receptacle for pressure sensitive application to the handle of any electrosurgical instrument;

FIG. 3 is a perspective view of an embodiment of the mechanical connector shown in FIG. 1 attached to the back of the hands witch;

FIG. 4 is a perspective view with partial cutaway of the mechanical connector shown in FIG. 1 viewed from the button side of the hands witch through the hands witch support;

FIG. 5 is a partial view of one half of the mechanical connector shown in FIG. 1, on edge, enlarged to detail the layers of the adjustable laminate of the tab;

DETAILED DESCRIPTION

Figure 1:
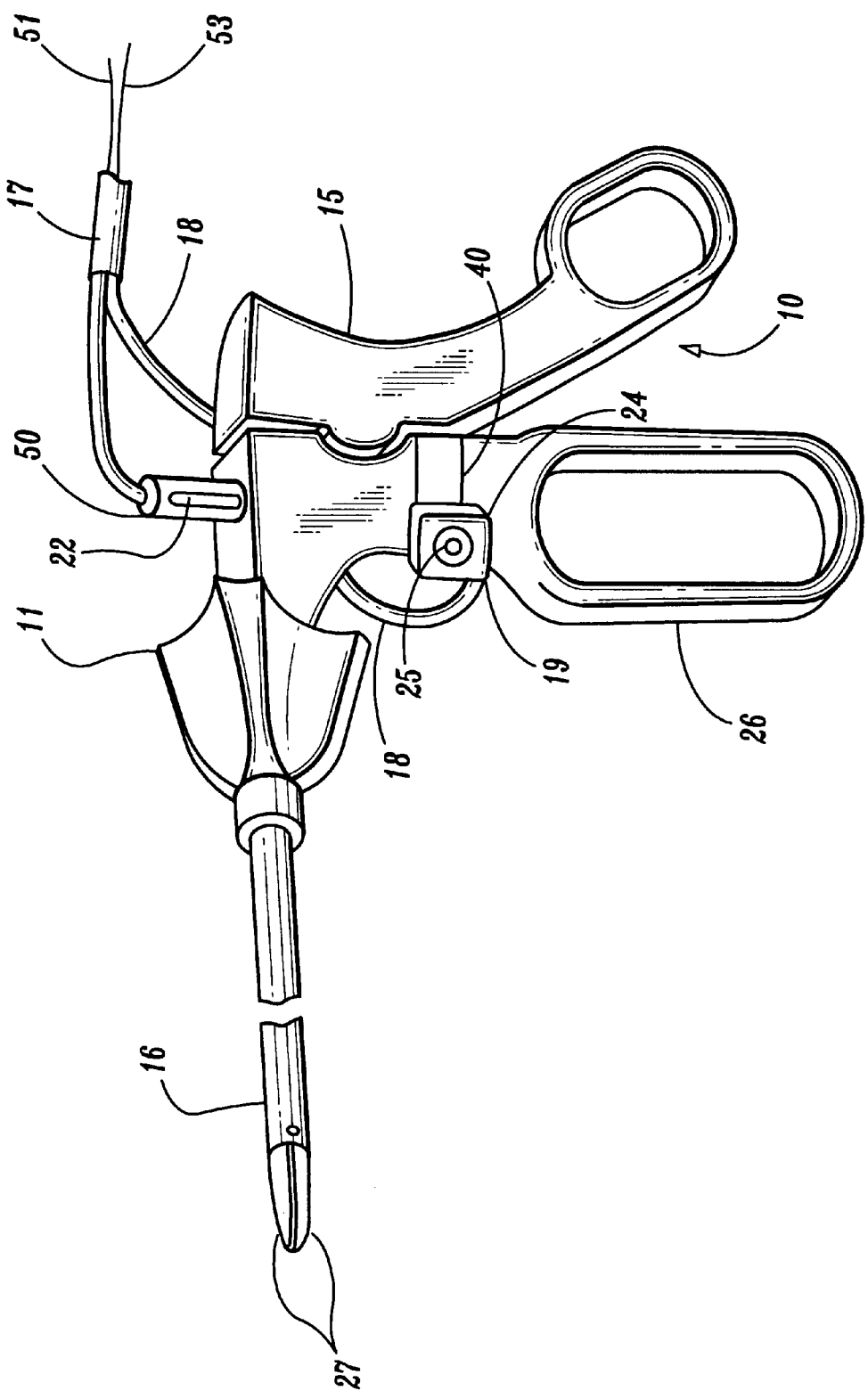
FIG. 1 is a perspective side view of one embodiment of the replaceable accessory cord and hands witch set.

A replaceable accessory cord and hands witch set 10 for use with an electrosurgical instrument 11 by a surgeon on a patient 12 in an electrosurgical circuit 13 is shown in FIGS. 1, 2, 6, 7, 8, 9, 12, and 13. The electrosurgical circuit 13 connects between an electrosurgical generator 14 and the electrosurgical instrument 11. The electrosurgical instrument 11 is an example of conventional instruments which are not manufactured with resident switches for activation of electrosurgical current. The electrosurgical instrument 11 has a proximal end 15 with an insulated handle 26 for holding by the surgeon and a distal end 16 which delivers electrosurgical current to the patient 12 through an end effector 27 such as scissors, graspers, or forceps.

An accessory cord 17 in FIGS. 1, 2, 6, 7, 8, 9, 12, and 13 is used in place of a standard replaceable cord and electrically connects the clectrosurgical general 14 to the electrosurgical instrument 11. The accessory cord 17 houses various conductors 51, 53, 54, and 60 which carry either RF or activation current. The accessory cord 17 additionally connects via a switch cord 18 to a hands witch 19 which mounts on the instrument 11 and actuates the electrosurgical current. The switch cord 18 houses various conductors 51, 51a, 51b, 52, and 60 which carry activation current. In alternate embodiments shown in FIGS. 6, 7, 8, 9, 12, and 13, the accessory cord 17 may connect with a connector 50 via a connector cord 59. The connector cord 59 may house conductors 53 and 54. The accessory cord 17, the switch cord 18, and the connector cord 19 are composed of, for example, polyvinylchloride. The various conductors 5,51a, 51b, 52, 53, 54, and 60 are composed of a conductive metallic wire such as, for example, copper and said conductors are insulated, for example, with a polyolefin coating.

A hands witch support 24 as in FIGS. 1, 3, 4, and 6 through 13, houses first and second hands witch contacts 20 and 21. The hands witch support 24 may be boxlike with a front, back, and four additional sides; the edges where the sides meet may be smooth and rounded. The hand switch support 24 is composed of, for example, a nonconductive, inexpensive molded thermoplastic, such as polycarbonate. The hand switch support 24 is also coated with polyurethane. The hand switch support 24 is electrically insulated from the first and second hand switch contacts 20 and 21, the instrument terminal 22, the instrument return terminal 23, and the conductors in the accessory cord 17. The first and second hand switch contacts 20 and 21 are inside the hand switch support 24 and may be mounted on ABS plastic.

An operating button 25 on the hand switch support 24 is accessible to the surgeon. The operating button 25 is composed of polycarbonate and is electrically isolated from the first and second hand switch contacts 20 and 21, and the conductors in the switch cord 18. The operating button 25 moves relative to the hand switch support 24. To apply electrosurgical current to the patient 12, the surgeon's finger presses the operating button 25, thereby closing the first and second hand switch contacts 20 and 21. Alternative plastic compositions of the hand switch support 24, the operating button 25, the accessory cord 17, the switch cord 18, the connector cord 59, and the insulators for the various conductors 51, 51a, 51b, 52, 53, 54, and 60 may be selected from available dielectric materials.

In FIG. 2, the hand switch support 24 is backed by a pressure sensitive adhesive 44 to mechanically connect the hand switch 19 to the instrument handle 26 preventing relative movement therebetween. This provides access to the hand switch 19 by a finger of the surgeon. The mechanical connection of the hand switch 19 is a mechanical connector 40 which appears in FIGS. 1 and 6 through 13, and is best shown in FIGS. 3, 4, AND 5. The mechanical connector 40 has two wing-like extensions, or tabs 65, which adjustably wrap around and conform to various parts and surfaces of the electrosurgical instrument 11, generally on the instrument handle 26. The mechanical connector 40 is a thin laminate composed of insulating tape 41, a sheet of malleable metal 42, additional insulating tape 43, adhesive 44, and a release liner 45. The malleable metal 42 can be copper, aluminum, steel, or any other metal with a modulus of elasticity in tension between 20 and 20 millions of pounds per square inch. The malleable metal 42 provides stiffness and tear resistance, as well as conformability, and in conjunction with the adhesive 44, prevents longitudinal, lateral, and circumferential movement of the hand switch 19 relative to the instrument 11. The insulating tape 41 and 43 is "3M 7331" polyester tape, the adhesive 44 is "3M 9472" adhesive, the release liner 45 is "3M 4994" release liner, (as manufactured by the 3M Corporation of Minneapolis, Minn.), and the malleable metal 42 is 0.005 mils thick annealed or soft copper. Skilled artisans will appreciate that other forms for the metallic layer, such as wire, mesh, screen, or the like, could be used.

The mechanical connector 40 is attached to the back of the hand switch support 24, by such as, for example, an ultrasonic weld. The mechanical connector 40 is perforated to accept rivets 47. The mechanical connector 40 is placed between the hand switch support 24 and a weld plate 46 with molded rivets 47, the weld plate 46 and rivets 47 are composed of polycarbonate. The rivets 47 are placed through the perforations in the mechanical connector 40 and are ultrasonically welded to the hand switch support 24, thereby clamping the mechanical connector 40 between the weld plate 46 and the hand switch support 24. Additional means of attachment of the mechanical connector 40 to the hand switch support 24, such as by adhesives, should be obvious to those skilled in the art.

Figure 6:
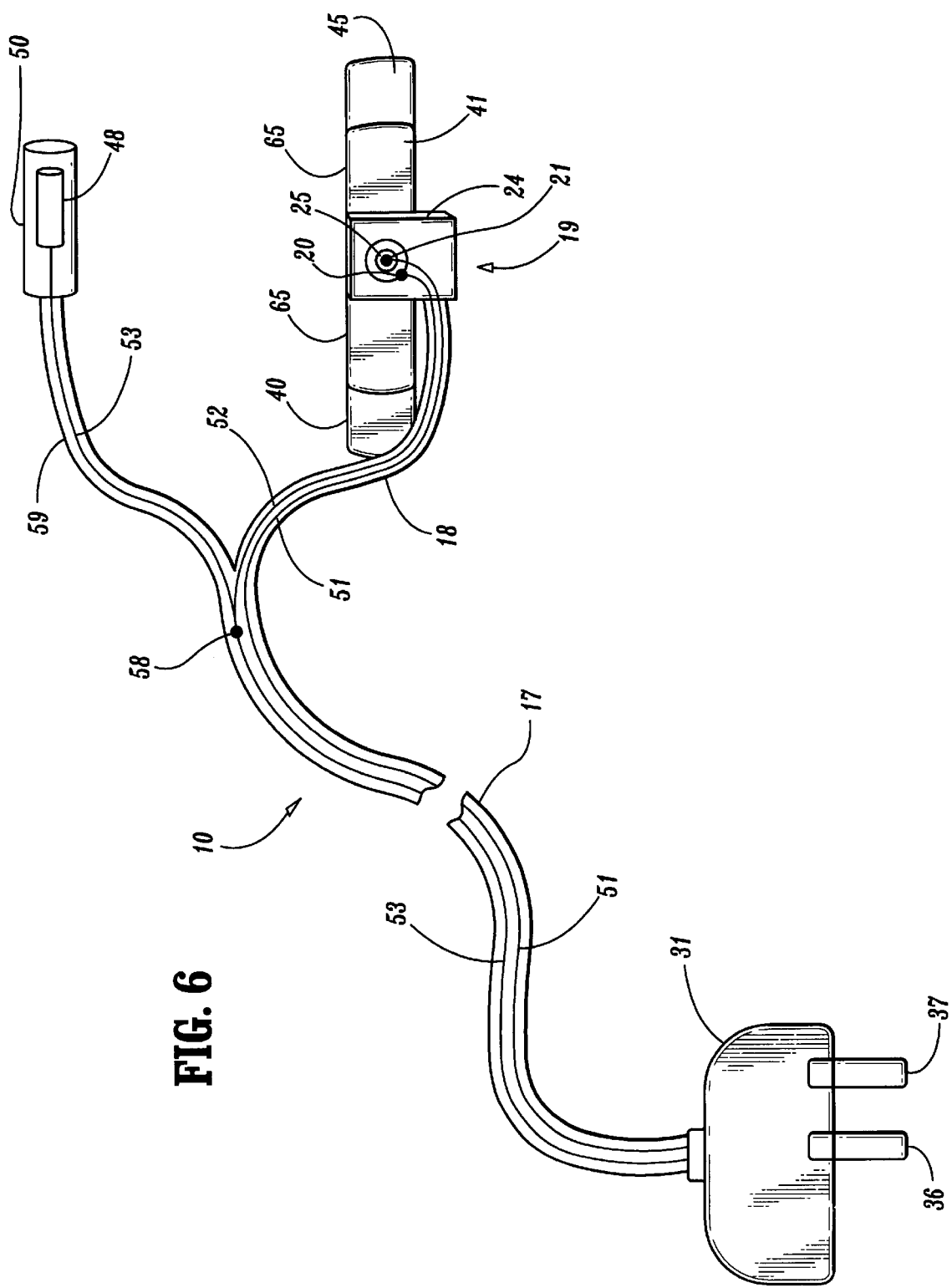
FIG. 6 is a perspective view with partial cutaway of the replaceable accessory cord and hands witch set for use with a monopolar electrosurgical instrument.
Figure 7:
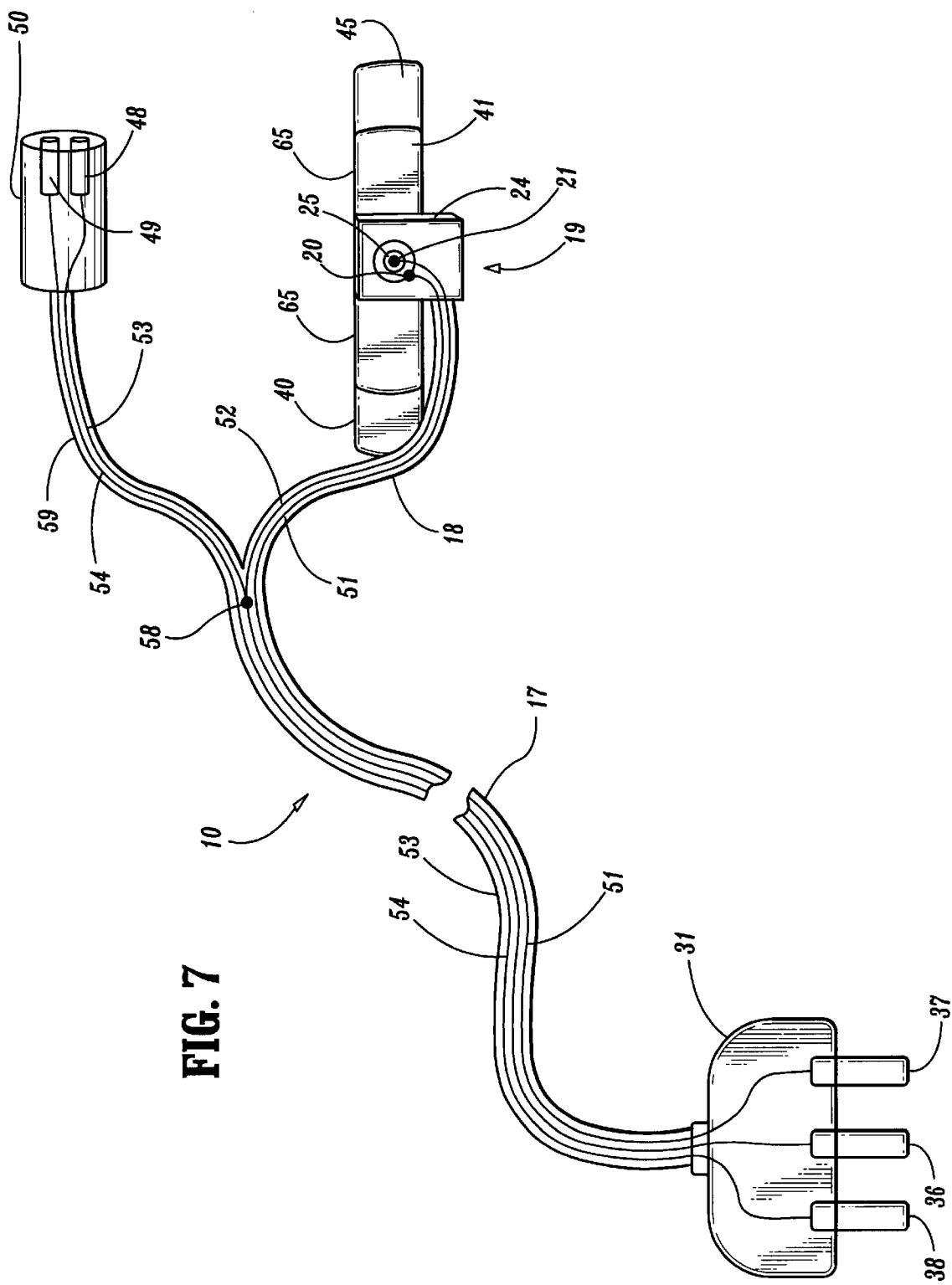
FIG. 7 is a perspective view with partial cutaway of the replaceable accessory cord and hands witch set for use with a bipolar electrosurgical instrument.
Figure 8:
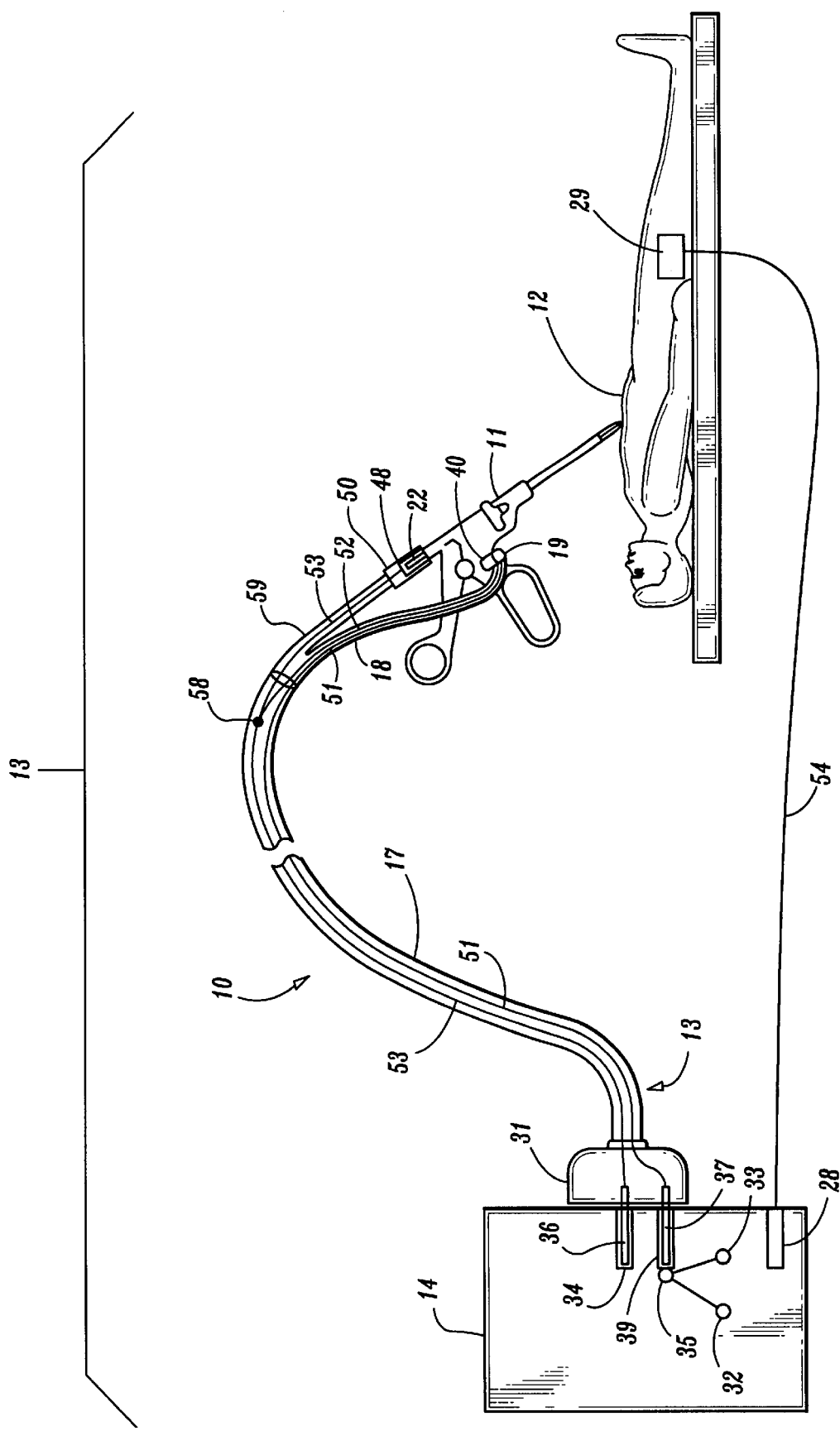
FIG. 8 is a perspective view with partial cutaway of the replaceable accessory cord and hands witch set as part of the complete monopolar electrosurgical circuit between the electrosurgical generator and the electrosurgical instrument.

For use with monopolar electrosurgical instruments, as in FIGS. 6 and 7, the first end of the replaceable accessory cord 17 may have plug 31 with at least first and second contacts, a plug RF contact 36 and a plug activation return contact 37, respectively, for electrically coupling with the electrosurgical generator 14, at the RF current output 34 and the activation current input 39, respectively. Within the accessory cord 17 are first and second conductors, an RF conductor 53 and an activation current return conductor 51, respectively, which electrically couple with the plug RF contact 36 and the plug activation return contact 37, respectively. The RF conductor 53 supplies high voltage electrosurgical current (also known as "RF current ") to the electrosurgical instrument 11 and also carries a low voltage activation current. The activation current controls the discharge of RF current by the electrosurgical generator 14 to the electrosurgical instrument 11. The activation current return conductor 51 provides the return path for the activation current from the hand switch 19 to the electrosurgical generator 14.

The second end of the replaceable accessory cord 17 may split into a connector cord 59 and a switch cord 18. The connector cord 59 has at least a first conductor, the RF conductor 53, electrically coupled with a first contact, a connector RF contact 48 within the connector 50, for electrically coupling the RF conductor 53 with a terminal 22 on the electrosurgical instrument 11. The switch cord 18 has at least first and second conductors, a switch conductor 52 and the activation current return conductor 51, respectively. The switch conductor 52 electrically couples with the RF conductor 53 within the accessory cord 17 at a RF-switch junction 58 and the activation current flows through the switch conductor 52. The switch conductor 57 electrically couples with the first hand switch contact 20 in the hand switch 19. The activation current return 51 electrically couples with the second hand switch contact 21 in the hand switch 19.

When the hand switch button 25 is depressed by the surgeon, the electrical switch created by the first and second hand switch contacts 20 and 21 is closed and the activation current flows from the switch conductor 52, through first and second hand switch contacts 20 and 21, and through the activation current return 51 to the generator 14. A reference in the electrosurgical generator 14 monitors continuity across the first and second hand switch contacts 20 and 21. When continuity is detected, the electrosurgical current is activated. Another scheme for power control is disclosed in U.S. pat. No. 3,752,160 which is hereby incorporated by reference. When using a monopolar instrument as in FIG. 8, the return path for the electrosurgical current passing through the end effectors 27 of the electrosurgical instrument 11 is through the patient 12, then through a return electrode 29 adhered to the patient 12, which is finally electrically coupled to a RF return conductor 54 returning to the electrosurgical generator 14 at the RF return input 28.

Figure 9:
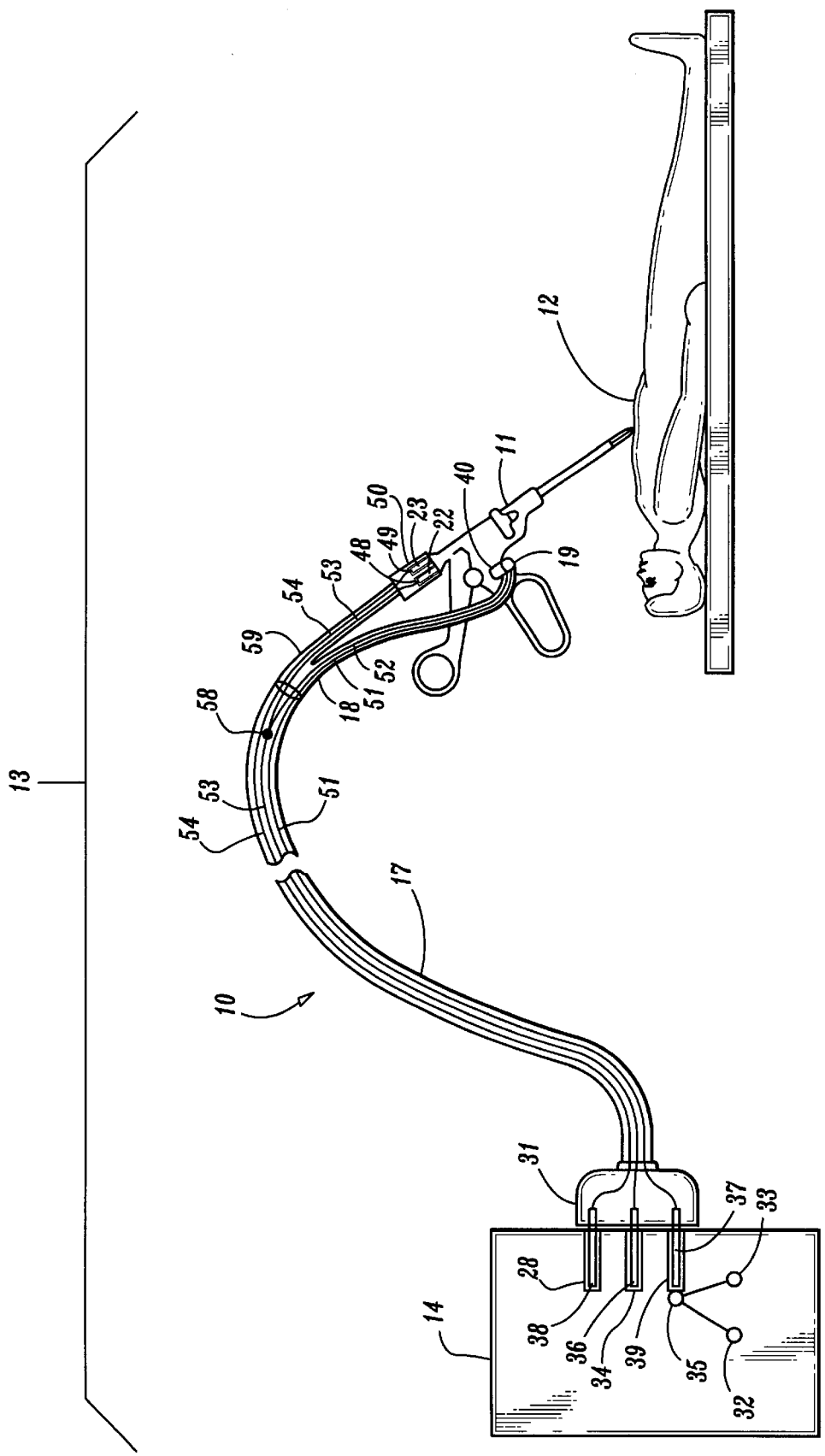
FIG. 9 is a perspective view with partial cutaway of the replaceable accessory cord and hands witch set as part of the complete bipolar electrosurgical circuit between the electrosurgical generator and the electrosurgical instrument.

Bipolar electrosurgical instruments as in FIGS. 7 and 9 typically have first and second contacts, a terminal 22 for supplying electrosurgical current to the instrument, and a return terminal 23 for returning the electrosurgical current to the electrosurgical generator 14. For use with bipolar instruments, the replaceable accessory cord may have a third conductor, such as, for example, an RF return conductor 54. On the first end of the accessory cord, the RF return conductor 54 electrically couples with a third contact, a plug RF return contact 38, the plug RF return contact 38 electrically coupling with the RF return input 28 on the electrosurgical generator 14. The RF return conductor 54 would continue through the connector cord 59 and electrically couple with a connector RF return contact 49 within the connector 50, the connector RF return contact 49 electrically coupling with the return terminal 23. In the bipolar configuration, the RF conductor 53, the switch conductor 52, and RF switch junction 58, the activation current return conductor 51, and the first and second hand switch contacts 20 and 21, all function as in the monopolar circuit. When using a bipolar electrosurgical instrument, the RF current travels through the electrosurgical instrument 11 to the end effectors 27 and then returns through the instrument 11 rather than through the patient 12 as in the monopolar circuit. The RF return conductor 54 within the accessory cord 17 is the return path for the electrosurgical current.

Figure 10:
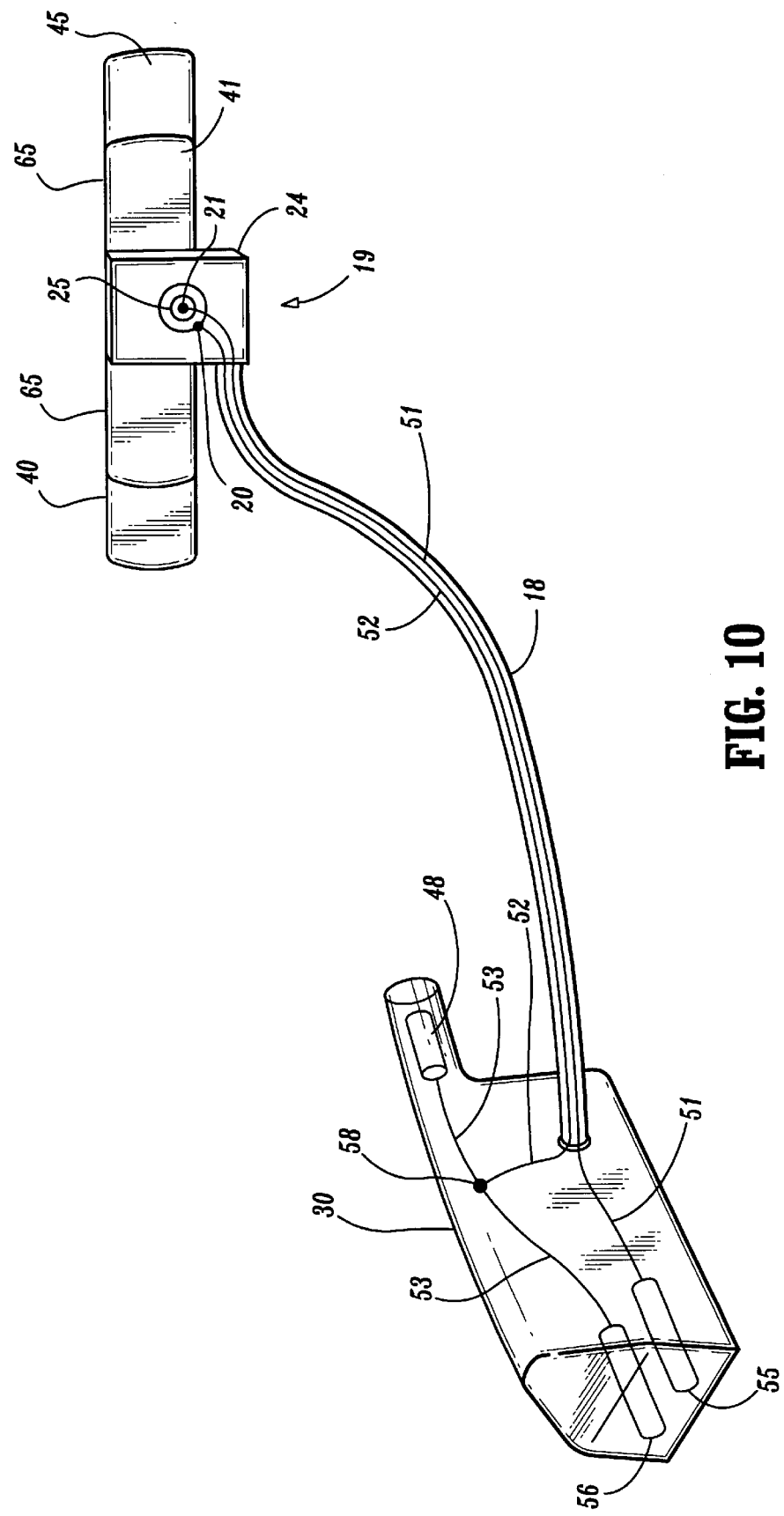
FIG. 10 is a perspective view with partial cutaway of an alternate embodiment for a jumper hands witch set for use with a reusable generator cord and a monopolar electrosurgical instrument.
Figure 11:
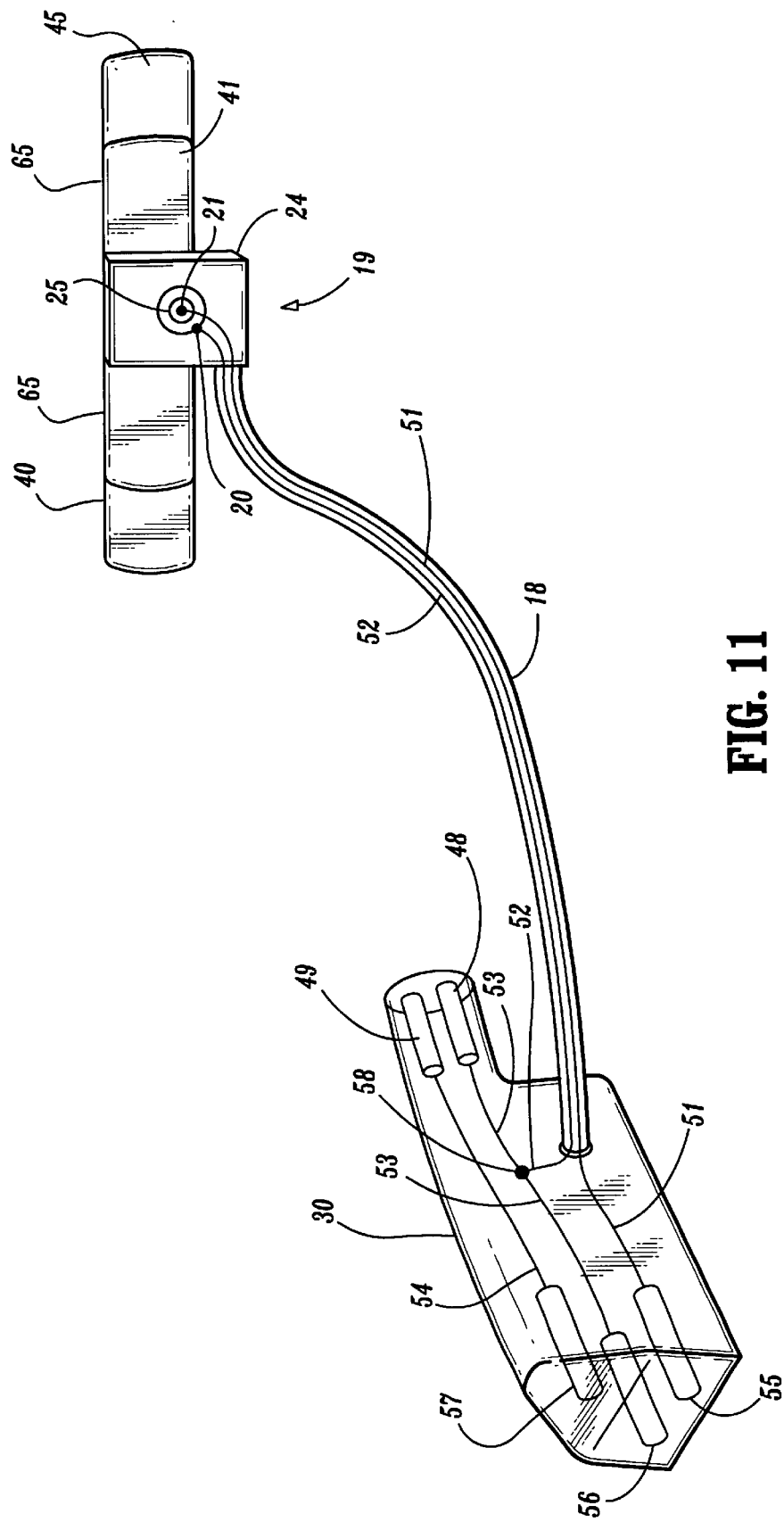
FIG. 11 is a perspective view with partial cutaway of an alternate embodiment for a jumper hands witch set for use with a reusable generator cord and a bipolar electrosurgical instrument.

While the accessory cord 17 is shown permanently attached to the hand switch 19 in the FIGS. 1, 2, 6, 7, 8, 9, 12, andl 3, skilled artisans will know that a removable connector such as a jumper 30 in FIGS. 10 and 11, could be used to allow the separation of the accessory cord 17 and the hand switch 19. The jumper 30 is an alternative embodiment which allows for connection of the hand switch 19 with a reusable accessory cord. The jumper 30 is composed of, for example, polyurethane surrounding ABS plastic upon which several contacts 48, 49, 55, 56 and 57 are mounted. In the monopolar configuration houses on a first end first and second contacts, a jumper switch contact 55 and a jumper RF contact 56, respectively. The jumper switch contact 55 electrically couples with the activation current return conductor 51 in a reusable accessory cord and with the activation current return conductor 51 in the switch cord 18. The jumper RF contact 56 electrically couples with the RF conductor 53 in a monopolar reusable accessory cord and with the connector RF contact 48, which in this embodiment is housed in the jumper 30. The jumper RF contact 56 also electrically couples with the switch conductor 52 in the switch cord 18. The switch cord 18 and its conductors 51a nd 52 electrically couple with the hand switch 19 as previously described.

In the bipolar configuration of FIG. 11, the jumper 30 has an additional contact, a jumper RF return contact 57, on the first end. The jumper RF return contact 57 electrically couples with the RF return conductor 54 in a bipolar reusable accessory cord and with the connector RF return contact 49, which in this embodiment is housed in the jumper 30.

A typical electrosurgical generator 14 creates first and second types of electrosurgical current waveforms, cutting and coagulation ("coag"), respectively. Cutting and coag waveforms differ in their shapes and tissue effects. Typically the plug 31 and the electrosurgical generator 14 in a monopolar circuit have first, second, and third conjugating connections, the first for a cut activation current, the second for a coag activation current, and the third for RF current. The embodiments described thus far have considered activation of only one type of current waveform, either cutting or coag, by the hand switch 19 and have referred to activation of either through the singular use of the term "activation current." Depending upon the configuration of the plug 31, i.e., whether the plug activation return contact 37 is electrically coupled with an activation current input 39 which is cut or an activation current input 39 which is coag, the hand switch 19 may activate either a cutting current waveform or coagulation current waveform.

In an alternative embodiment of the replaceable accessory cord and hand switch set 10, the plug 31 may have an additional contact and the accessory cord 17 and switch cord 18 may have an additional conductor to differentiate between cut and coag return current. For example, there may be first and second activation return conductors, a cut return conductor 51a and a coag return conductor 51b, respectively, as shown under different circumstances in FIGS. 12 and 13. A cut-coag switch 35 could then be created by splitting the hand switch button 25 into a cut button 25a and a coag button 25b, see FIGS. 12 and 13, or substitute a rocker button as in common on electrosurgical pencils with integral switching. The cut-coag switch 35 could similarly be integrated on the plug 31, along the accessory cord 17, or within the electrosurgical generator 14. See FIGS. 8 and 9.

Figure 12:
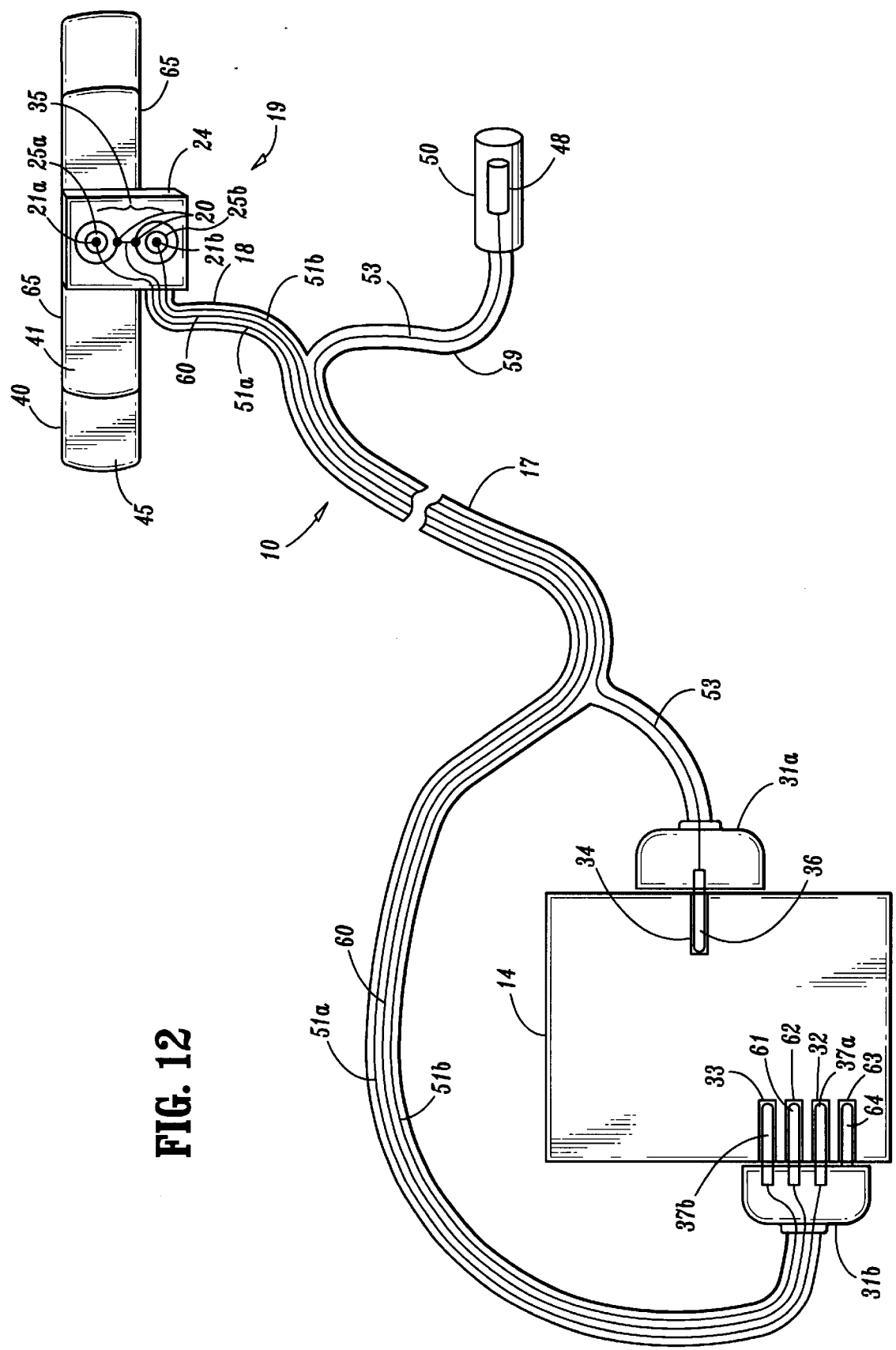
FIG. 12 is a perspective view with partial cutaway of an alternate embodiment of the replaceable accessory cord and hands witch set for use in place of a standard footswitch and with a monopolar electrosurgical instrument.
Figure 13:
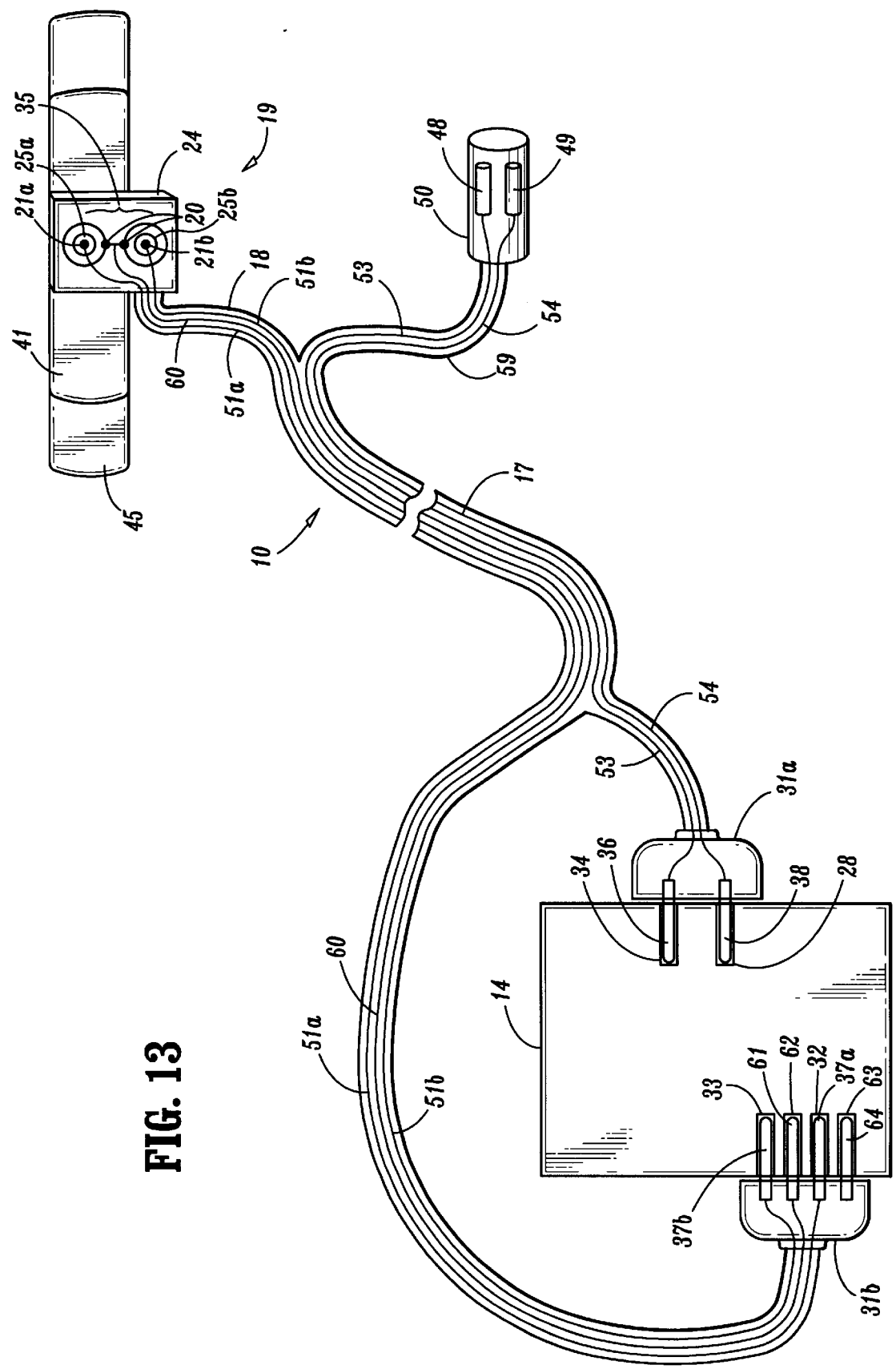
FIG. 13 is a perspective view with partial cutaway of an alternate embodiment of the replaceable accessory cord and hands witch set for use in place of a standard footswitch and with a bipolar electrosurgical instrument.

An alternative embodiment of the replaceable accessory cord and hand switch set 10 for use with an electrosurgical generator 14, the electrosurgical generator 14 without hand switch contacts, but having footswitch contacts (e.g., certain neurosurgery model generators), is shown in FIGS. 12 and 13. When using the footswitch contacts to activate a hand switch 19, the RF current and the activation current are isolated. Therefore, an additional conductor, an activation current conductor 60, are employed in the accessory cord 17 and switch cord 18, and a separate RF plug 31a is used to electrically couple the RF conductor 53 and plug RF contact 36 with the RF current output 34. The activation current conductor 60 electrically couples on the first end to an activation current contact 61 in a footswitch plug 31b. The activation current contact 61 electrically couples with the activation current output 62 on the electrosurgical generator 14. The second end of the activation current conductor 60 electrically couples with the first hand switch contact 20 in the hand switch 19. In this embodiment the hand switch 19 has first and second hand switch buttons, a cut button 25a and a coag button 25b, respectively. The first hand switch contact 20 is common to both the cut button 25a and the coag button 25b.

When the cut button 25a is depressed by the surgeon, electrical contact is made between the first hand switch contact 20 and the cut hand switch contact 21a. The cut hand switch contact 21a is electrically coupled with a cut return conductor 51a, the cut return conductor 51a similarly electrically coupled with a cut return contact 37a in the footswitch plug 31b. The cut return contact 37a electrically couples with the cut signal contact 32 in the electrosurgical generator 14. Similarly, when the coag button 25b is depressed by the surgeon, electrical contact is made between the first hand switch contact 20 and the coag hand switch contact 21b. The coag hand switch contact 21b is electrically coupled with a coag return conductor 51b, the coag return conductor 51b similarly electrically coupled with a coag return contact 37bin the footswitch plug 31b. The coag return contact 37b electrically couples with the coag signal contact 33 in the electrosurgical generator 14.

Typically footswitch receptacles have a fourth input contact, a footswitch ground input 64, for a ground conductor from a footswitch to prevent a short, a footswitch being composed of metal and placed on the floor. The hand switch 19, being completely electrically insulated, has no need for an additional ground conductor. The footswitch plug 31b may provide a fourth contact, a footswitch ground contact 63, the footswitch ground contact 63 not electrically connected to any conductor, but simply holding a place and proving a more secure mechanical connection between the footswitch plug 31b and the electrosurgical generator 14.

It will be understood that various modifications may be made to the embodiments disclosed herein. Therefore, the above description should not be construed as limiting, but merely an exemplification of preferred embodiments. Those skilled in the art will envision other modifications within the scope and spirit of the claims appended hereto.

What is claimed is:

1. A replaceable accessory cord and hands witch set for use with an electrossurgical instrument, the clectrosurgical instrument having a distal end for delivery therefrom of electrosurgical current to a patient, and a proximal end for holding by a surgeon, the proximal end having a terminal for connecting with the replaceable accessory cord and hands witch set for receiving clectrosurgical current, the replaceable accessory cord and hands witch set comprising:

an accessory cord having a least first and second conductors, the accessory cord including at least one split end defining a conductor cord independently connected to a connector and a switch cord independently connected to a handswitch, the hands witch electrically coupled to the first conductor, for mounting on the proximal end of the electrosurgical instrument for access by the surgeon;

first and second contacts in the handswitch, the contacts normally open, the first contact attached to the first conductor and the second contact connected to the second conductor;

a receptacle on the hands witch connected electrically to the second contact, the receptacle configured to conjugate with the terminal when mounted on the electrosurgical instrument through an RF switch junction and the conductor cord on the electrosurgical instrument;

a support on the hands witch for adjustable mechanical connection, the mechanical connection configured to adapt with the electrosurgical instrument by flexibly conforming to a portion the electrosurgical instrument to prevent movement relative thereto, the support electrically insulated from the pair of contacts, the receptacle, the terminal and the conductors, and an operating button on the support accessible to the surgeon, the operating button positioned remotely from the receptacle and the terminal so that the operating button is convenient to the surgeon, the operating button electrically isolated from the pair of contacts, the receptacle, the terminal and the conductors, the operating button movably mounted to the support for closing the pair of contacts during use of the Clectrosurgical instrument when applying electrosurgical energy to the patient.

2. The replaceable accessory cord and hands witch set of claim 1 adapted for use with a handle on the electrosurgical instrument for use by the surgeon and one or more end effectors on the electrosurgical instrument for application of electrosurgical energy and wherein the support and operating button are adapted to be physically located on the handle so when the electrosurgical instrument is grasped by the handle, the operating button is positioned for control of electrosurgical energy delivery by the surgeon's finger.

3. The replaceable accessory cord and hands witch set of claim 2 wherein the handswitch on the handle is insulated and is adapted to be mounted at the proximal end of the electrosurgical instrument and one or more electrosurgical effectors is located opposite the handle at the distal end of the electrosurgical instrument.

4. The replaceable accessory cord and handswitch set of claim 2 wherein the handswitch is adapted to be electrically connected with the one or more end effectors in a bipolar circuit and a return is located on one of the end effectors and is connected to one of the conductors for completing the electrosurgical circuit.

5. The replaceable accessory cord and handswitch set of claim 2 wherein the handswitch is adapted to be electrically connected with the one or more end effectors in a monopolar circuit and a return pad is on the patient in the electrosurgical circuit.

6. The replaceable accessory cord and handswitch set of claim 2 wherein the receptacle adaptively conjugates with the terminal positioned near the proximal end of the electrosurgical instrument for minimizing the size and bulk of the support.

7. A replaceable handswitch adapted for use with an electrosurgical instrument for use by a surgeon on a patient in an electrosurgical circuit adapted to connect between an electrosurgical generator, the electrosurgical instrument and the patient, the electrosurgical instrument has a proximal end for holding by the surgeon and a distal end for delivery therefrom of electrosurgery to the patient, the electrosurgical circuit includes a cord for electrically coupling to the electrosurgical generator to supply electrosurgery to the replaceable handswitch, the cord having two or more conductors, the replaceable handswitch comprising:

a pair of normally open contacts in the handswitch so one contact is electrically coupled to an active conductor, the pair of contacts mounted near the proximal end of the electrosurgical instrument for access by the surgeon, the handswitch in the electrosurgical circuit so another conductor from the electrosurgical generator is connected to the other contact;

an RF conductor connected to at least one contact for supplying a high voltage electrosurgical current to the electrosurgical instrument, the RF conductor also supplying a low voltage activation current;

a receptacle on the handswitch connected electrically to the contact, the receptacle configured to mount to the electrosurgical instrument and electrically couple with a terminal positioned on the surgical instrument, the terminal in electrical contact with the active conductor;

a support on the handswitch configured for mounting on the electrosurgical instrument to prevent movement relative thereto, the support electrically insulated from the pair of contacts, the receptacle, the terminal and the conductors, the support attached to a mechanical connector including a flexible adhesive wrap configured to securely conform to and adapt with a portion of the electrosurgical instrument, and an operating button on the support accessible to the surgeon, the operating button positioned remotely from the receptacle and the terminal, the operating button electrically isolated from the pair of contacts, the receptacle, the terminal and the conductors, the operating button movably mounted relative to the support for closing the pair of contacts to apply electrosurgical energy during the use of the instrument to the patient.

8. The replaceable handswitch adapted for use with the electrosurgical instrument of claim 7, wherein a jumper having a jumper switch contact and a jumper RF contact, the jumper switch being electrically coupled with the handswitch, the jumper RF contact being electrically coupled with a RF conductor and a switch conductor.

9. The replaceable handswitch adapted for use with the electrosurgical instrument of claim 8, wherein the jumper includes a RF switch junction.

10. A switch cord and handswitch for controlling an electrosurgical instrument, the switch cord and handswitch electrically adaptively coupled to an electrosurgical generator and the electrosurgical instrument, and adapted to be physically attached to the electrosurgical instrument, the electrosurgical generator capable of producing an electrosurgical current, the switch cord and handswitch comprising:

a handswitch having a handswitch button adapted for electrically controlling the electrosurgical generator to activate or stop electrosurgical current flow to the electrosurgical instrument;

a switch cord extending from the handswitch, the switch cord having at least first and second conductors, the conductors in an electrical circuit with the handswitch button, the electrosurgical generator and the electrosurgical instrument; and a mechanical connector attached to the handswitch for supporting the handswitch mounted on the electrosurgical instrument, the mechanical connector having at least two tabs extending beyond the dimensions of the handswitch, each tab including a laminate composed of at least an adhesive layer and a malleable metallic layer, the tabs configured to adapt to the electrosurgical instrument by securely conforming and adhering to a portion of the exterior surface of the electrosurgical instrument.

11. The switch cord and handswitch of claim 10 wherein the laminate composing the tabs of the mechanical connector includes an insulating tape layered on each side of the malleable metal.

12. The switch cord and handswitch of claim 10 wherein the laminate composing the tabs of the mechanical connector includes a release liner layered against the contact side of the adhesive.

13. The switch cord and handswitch of claim 11 wherein the laminate composing the tabs of the mechanical connector includes a release liner layered against the contact side of the adhesive.

14. A method of attaching a switch cord and handswitch via a mechanical connector to an electrosurgical instrument, the handswitch for activating the electrosurgical instrument connected to an electrosurgical generator via the switch cord, the switch cord extending from the handswitch, the electrosurgical generator capable of supplying electrosurgical current, the handswitch having a handswitch button for electrically controlling the electrosurgical generator to activate or stop electrosurgical current flow to the electrosurgical instrument, the switch cord having at least first and second conductors in an electrical circuit with the handswitch button, the electrosurgical generator and the electrosurgical instrument, the mechanical connector attached to the handswitch for supporting the electrosurgical instrument, the mechanical connector having at least two tabs extending beyond the dimensions of the handswitch, each tab including a laminate composed of at least an adhesive layer and a malleable metallic layer, the mechanical connector sized relative to the electrosurgical instrument for securely conforming and adhering to the electrosurgical instrument, the method of attaching the switch cord and handswitch with the steps of:

conforming the malleable metallic layer of the tabs of the mechanical connector to the electrosurgical instrument; and adhering the adhesive layer of the tabs of the mechanical connector to the electrosurgical instrument.

* * * * *